United States Patent [19]

Schubert et al.

[11] Patent Number: 5,081,133
[45] Date of Patent: Jan. 14, 1992

[54] 2-ANILINOCYANOPYRIDINES HAVING FUNGICIDAL PROPERTIES

[75] Inventors: Juergen Schubert, Mannheim; Jochen Wild, Deidesheim; Albrecht Harreus, Ludwigshafen; Thomas Kuekenhoehner, Frankenthal; Hubert Sauter, Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 470,309

[22] Filed: Jan. 25, 1990

[30] Foreign Application Priority Data

Feb. 21, 1989 [DE] Fed. Rep. of Germany ....... 3905238

[51] Int. Cl.$^5$ ............... C07D 213/74; C07D 213/85; A01N 43/40
[52] U.S. Cl. .................... 514/344; 546/286; 546/287; 546/289
[58] Field of Search ......... 546/286, 287, 289; 71/94; 514/344

[56] References Cited

U.S. PATENT DOCUMENTS 4,331,670 5/1982 Nishiyama et al. ............. 514/349
4,395,555 7/1983 Acker et al. ..................... 546/289

FOREIGN PATENT DOCUMENTS 3528459 8/1985 Fed. Rep. of Germany ...... 546/287

OTHER PUBLICATIONS

March, Advanced Organic Chemistry, Second Edition, pp. 460–466, McGraw-Hill Pub. QD 251 M2 1977, C.5.
Jerry March, Advanced Organic Chemistry Reactions, Mechanisms, and Structure, Third Edition, pp. 598–600, 1086–1087, 1089–1090, 1985, New York, N.Y.
Alan R. Katritzky, Handbook of Heterocyclic Chemistry, pp. 145–146, 1985, New York, N.Y.
Jerry March, Advanced Organic Chemistry Reactions, Mechanisms, and Structure, SEcond Edition, pp. 658–659, 1977, New York, N.Y.
CRC Handbook of Chemistry and Physics, 64th Edition, C-488-9, C-90-160, 1983-1984, Boca Raton, Fla.

Primary Examiner—Alan L. Rotman
Attorney, Agent, or Firm—Oblon, Spivak, McClelland, Maier & Neustadt

[57] ABSTRACT

2-Anilinocyanopyridines of the formula

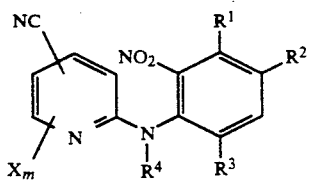

where
X is $NO_2$, CN, halogen, $SO_2$-alkyl, alkyl, cycloalkyl, haloalkyl, alkoxy, or phenoxy or phenylthio which is unsubstituted or substituted in the phenyl,
m is an integer from 1 to 3,
$R^1$ is hydrogen, halogen, alkoxy, haloalkyl, haloalkoxy, or phenoxy or phenylthio which is unsubstituted or substituted in the phenyl,
$R^2$ and $R^3$ are hydrogen, $NO_2$, halogen, CN, alkyl, $SO_2$-alkyl, haloalkyl, $SO_2NR^5R^6$, haloalkoxy, $COOR^5$ or $CONR^5R^6$,
$R^4$ is hydrogen, $COOR^7$, $CONR^5R^6$, CHO, $COR^7$, $SO_2R^7$, $C_3$–$C_6$-alkenyl or $C_3$–$C_6$-alkynyl, and salts of these 2-anilinocyanopyridines of the formula I in which $R^4$ is hydrogen with plant-tolerated cations, and fungicides containing these compounds.

8 Claims, No Drawings

2-ANILINOCYANOPYRIDINES HAVING FUNGICIDAL PROPERTIES

The present invention relates to novel, valuable 2-anilinocyanopyridines, processes for the preparation thereof, fungicidal agents containing these compounds and the use thereof as fungicides.

It has been disclosed that 2-anilinopyridines, for example 2-(2,4-dinitro-6-trifluoromethylanilino)-5-trifluoromethylpyridine (EP-A 31 257) have a good fungicidal action. However, the action is not always satisfactory at low application rates and use concentrations.

We have now found, surprisingly, that 2-anilinocyanopyridines of the formula I

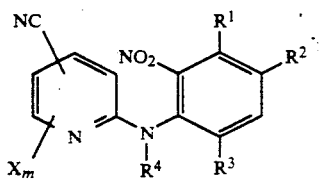

where
X is $NO_2$, CN, halogen, $SO_2$—$C_1$-$C_4$-alkyl, $C_1$-$C_4$-alkyl, $C_3$-$C_6$-cycloalkyl, $C_1$-$C_4$-haloalkyl, $C_1$-$C_4$-alkoxy, or phenoxy or phenylthio which can be substituted in the phenyl,
m is an integer from 1 to 3, with the individual radicals being identical or different when m is greater than 1,
$R^1$ is hydrogen, halogen, $C_1$-$C_4$-alkoxy, $C_1$-$C_4$-haloalkyl, $C_1$-$C_4$-haloalkoxy, or phenoxy or phenylthio which can be substituted in the phenyl,
$R^2$ and $R^3$ are, independently of one another, hydrogen, $NO_2$, halogen, CN, $C_1$-$C_6$-alkyl, $SO_2$—$C_1$-$C_4$-alkyl, $C_1$-$C_6$-haloalkyl, $SO_2NR^5R^6$, $C_1$-$C_4$-haloalkoxy, $COOR^5$ or $CONR^5R^6$,
$R^4$ is hydrogen, $COOR^7$, $CONR^5R^6$, CHO, $COR^7$, $SO_2R^7$, $C_3$-$C_6$-alkenyl or $C_3$-$C_6$-alkynyl,
$R^5$ and $R^6$ are, independently of one another, hydrogen or $C_1$-$C_4$-alkyl,
$R^7$ is $C_1$-$C_4$-alkyl, $C_1$-$C_4$-haloalkyl, benzyl, or aryl which can be substituted,
and salts of the 2-anilinocyanopyridines of the formula I in which $R^4$ is hydrogen with cations which are tolerated by plants, have a very good fungicidal action and are excellently tolerated by plants.

The term alkyl means, on its own or as part of another substituent such as haloalkyl, alkoxy or haloalkoxy, depending on the number of carbon atoms indicated, the following straight-chain or branched groups: methyl, ethyl, n-propyl, iso-propyl, n-butyl, sec-butyl, iso-butyl, tert-butyl, n-pentyl and n-hexyl. The prefix halo in the name of a substituent means, here and hereinafter, that this substituent can be mono- to perhalogenated. Halogen represents F, Cl, Br or I. Haloalkyl is thus a mono- to perhalogenated alkyl such as $CH_2Cl$, $CHCl_2$, $CCl_3$, $CH_2F$, $CHF_2$, $CF_3$, $CH_2Br$, $CHBrCl$, $CF_2Cl$, $C_2Cl_5$, $C_2F_5$, $CF_2$—$CHF_2$, $CH_2CH_2Cl$, $CH_2CH_2Br$, $C_3F_7$ or $C_4F_9$.

Cycloalkyl is cyclopropyl, cyclobutyl, cyclopentyl and cyclohexyl, it being possible for the rings to be substituted by one or two methyls, such as 1-methylcyclopropyl, 2-methylcyclopropyl, 2,2-dimethylcyclopropyl, 1-methylcyclopentyl or 1-methylcyclohexyl.

Examples of alkenyl are allyl, 3-butenyl, 4-butenyl, trans-2-butenyl and cis-2-butenyl.

Examples of alkynyl are propargyl, 3-butynyl, 4-butynyl and 5-pentynyl.

Examples of aryl which can be substituted are phenyl, 2-, 3- and 4-tolyl, halophenyl, 4-bromophenyl, 4-chlorophenyl, 4-fluorophenyl, nitrophenyl, 2-nitrophenyl, 4-nitrophenyl, and 1- and 2-naphthyl.

The meaning of phenoxy or phenylthio which can be substituted is that the aromatic ring is unsubstituted or can be halogenated one to three times, such as 2-Cl, 2-F, 3-Cl, 4-Cl, 4-Br, 2,3-$Cl_2$, 2,4-$Cl_2$, 2,5-$Cl_2$, 2,6-$Cl_2$, 3,5-$Cl_2$, 2,4,6-$Cl_3$ or 3,4,5-$Cl_3$, or can have one or two substituents such as nitro or methyl, for example 2-$NO_2$, 4-$NO_2$, 2-$CH_3$, 4-$CH_3$, 2,6-$(CH_3)_2$ or 3,5-$(CH_3)_2$.

Examples of suitable cations for the salts are the following: $Na^+$, $K^+$, $Mg^{2+}$, $Fe^{3+}$ and $NH_4^+$, ammonium cations which are alkylated, hydroxyalkylated and/or arylated one or more times, such as diisopropylammonium, tetramethylammonium, tetrabutylammonium, trimethylbenzylammonium, N,N-dimethylanilinium or trimethyl(2-hydroxyethyl)ammonium, where the alkyl has 1 to 4 carbon atoms and the aryl is phenyl or benzyl.

The compounds of the formula I as claimed in claim 1, in which $R^4$ is hydrogen, are prepared, for example, by reacting a cyanopyridine of the formula II

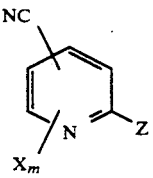

where X and M have the meanings specified in claim 1, with compounds of the formula III

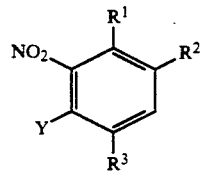

where $R^1$, $R^2$ and $R^3$ have the meanings specified in claim 1, as the substance or in a solvent or diluent, in the presence or absence of an organic or inorganic base, at from $-20°$ to $200°$ C., where Y and Z are $NH_2$ or halogen and Y and Z are different from one another.

In both cases the reaction takes place with elimination of hydrogen halide. It is therefore advantageous in both cases to use acid-binding agents or bases.

Bases or acid-binding agents which can be used are organic or inorganic compounds such as alkali metal and alkaline earth metal hydroxides (LiOH, NaOH, KOH, Ca(OH)$_2$), oxides (Na$_2$O, Li$_2$O, CaO, MgO), hydrides (LiH, NaH, KH, CaH$_2$), amides (LiNH$_2$, NaNH$_2$, KNH$_2$), carbonates (Li$_2$CO$_3$, Na$_2$CO$_3$, CaCO$_3$), bicarbonates (NaHCO$_3$), alkyls (butylLi, CH$_3$Li, CH$_3$MgCl), C$_1$-C$_5$-alcoholates (NaOCH$_3$, NaOC$_2$H$_5$, KOC$_2$H$_5$, KO-tert-butyl, Mg(OCH$_3$)$_2$) or amines, especially the tertiary amines (e.g. trimethylamine, triethylamine, diisopropylethylamine, N-methylpiperidine), pyridine, substituted pyridines (collidine, lutidines, 4-dimethylaminopyridine) or bicyclic amines.

The reactions can be carried out in the presence of solvents or diluents which are inert under the reaction conditions.

Suitable examples are aliphatic and aromatic hydrocarbons such as toluene, xylenes, cyclohexane and petroleum ether; halohydrocarbons such as chlorobenzene, methylene chloride and chloroform; ethers and ether-like compounds such as dialkyl ethers (diethyl ether, diisopropyl ether, tert-butyl methyl ether etc.), anisole, dioxane and tetrahydrofuran; nitriles such as acetonitrile, propionitrile, N,N-dialkylated amides such as dimethylformamide; dimethyl sulfoxide; ketones such as acetone, diethyl ketone and methyl ethyl ketone, alcohols such as methanol, ethanol, n- and isopropanol, butanols, especially tert-butanol, and mixtures of such solvents.

The reaction temperature can be varied within wide limits. Depending on the nature of the substituents X, $R^1$, $R^2$, $R^3$, $R^5$, $R^6$, $R^7$ and the number m thereof, the temperatures are from $-20°$ C. to $200°$ C. or the boiling point of the solvent or solvent mixture.

It may also be advantageous in some cases to carry out the reaction under an atmosphere of protective gas and/or in anhydrous solvents. Suitable protective gases are inert gases such as helium, argon etc., preferably nitrogen.

The starting compounds are commercially available or are known or can be prepared easily by conventional methods. The haloaromatic compounds (or phenols which can be easily converted into these) and anilines which are employed are commercially available.

Reference may be made to the following for 2-amino- and 2-halo-cyanopyridines: DE-A 31 03 065 and DE-A 35 28 459.

2-Amino- and 2-halo-cyanopyridines which have not yet been described can be prepared from substituted 2-hydroxypyridines or substituted pyridinecarboxylic acids by conventional methods of chemical synthesis. For example

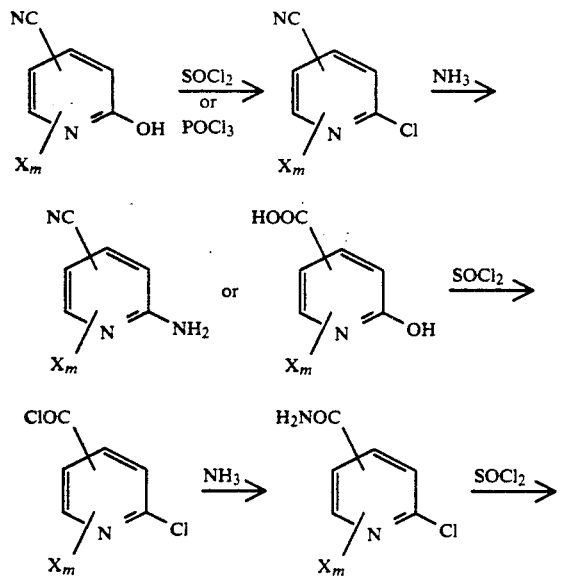

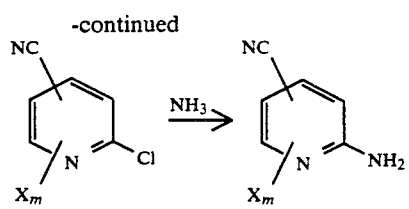

The compounds of the formula I, as claimed in claim 1 with the proviso that $R^4$ is not hydrogen, are prepared, for example, by reacting a cyanopyridine of the formula I in which $R^4$ is hydrogen, and X, m, $R^1$, $R^2$, $R^3$, $R^5$, $R^6$ and $R^7$ have the meanings specified in claim 1, with an alkylating, acylating or sulfonylating agent of the formula IV $$LR^4 \qquad\qquad IV$$

where $R^4$ has the meaning specified in claim 1 apart from hydrogen, and L is a leaving group which can be displaced nucleophilically, as the substance or in the presence of a solvent or diluent and in the presence or absence of an organic or inorganic base at from $-20°$ C. to $150°$ C.

Suitable and preferred groups which can be displaced nucleophilically are halogens such as F, Cl, Br and I, sulfonates (methanesulfonate, benzenesulfonate etc.), alcoholates (ethylate, benzylate etc.) and carboxylates (acetate etc.).

The bases which can be used are the same compounds used for the preparation of compounds of the formula I ($R^4$=H) from compounds of the formulae II and III.

The reaction temperatures are generally from $-20°$ C. to $150°$ C. or at the boiling point of the solvent or solvent mixture.

It is possible for one or more solvents or diluents which are inert under the reaction conditions to be present during the reaction. Suitable examples are aliphatic and aromatic hydrocarbons such as toluene, xylenes, cyclohexane and petroleum ethers; halohydrocarbons such as chlorobenzene, methylene chloride, ethylene chloride, chloroform and tetrachloroethylene; ethers and ether-like compounds such as dialkyl ethers (diethyl ether, diisopropyl ether, tert-butyl methyl ether etc.), anisole, dioxane and tetrahydrofuran; nitriles such as acetonitrile and propionitrile; N,N-dialkylated amides such as dimethylformamide; dimethyl sulfoxide; ketones such as acetone, diethyl ketone and methyl ethyl ketone, and mixtures of such solvents.

The novel compounds are isolated by conventional methods. The resulting products can be purified by recrystallization, extraction or chromatography. The examples which follow are intended to illustrate the preparation:

EXAMPLE 1

A solution of 56.6 g (0.51 mol) of potassium tert-butylate in 500 ml of tert-butanol is added dropwise within 1 h to a vigorously stirred suspension of 57.5 g (0.25 mol) of 2-amino-3,5-dicyano-6-ethoxy-4-isopropylpyridine and 83.8 g (0.275 mol) of 1,3-dichloro-2,6-dinitro-4-trifluoromethylbenzene in 600 ml of 1:1 tetrahydrofuran/tert-butanol at $0°$-$5°$ C. After 1 h at $0°$ C., the mixture is warmed to room temperature ($20°$ C.) within 2 h, and then acidified with glacial acetic acid (pH 4), diluted with 2 l of water and extracted 3 times with 50 ml of diethyl ether each time. The combined ether extracts are washed with saturated brine, dried over MgSO$_4$ and concentrated, and the residue is stirred with ethanol; 72 g (58% of theory) of compound 1.239 are obtained as yellow crystals of melting point 165°–167° C.

EXAMPLE 2

0.24 g (0.01 mol) of sodium hydride is added a little at a time to a solution of 3.4 g (0.01 mol) of 3-chloro-5-cyano-2-(2-nitro-4-trifluoromethylanilino)pyridine (compound 3.58) in 25 ml of tetrahydrofuran. After 15 min, 3.5 g (0.02 mol) of benzenesulfonyl chloride are added dropwise at room temperature. After 48 h at 60° C., 150 ml of water are added and the mixture is extracted 3 times with 100 ml of ether each time. The combined ether extracts are washed with saturated brine, dried over MgSO$_4$ and concentrated. The residue is chromatographed (silica gel, 9:1 cyclohexane/ethyl acetate). 1.5 g (31% of theory) of compound 5.12 are obtained as yellow crystals of melting point 147°–158° C.

The compounds described in the following Tables can be prepared using these methods.

TABLE 1

3-Cyanopyridine derivatives

| No. | X$_m$ | R$^1$ | R$^2$ | R$^3$ | m.p. (°C.) |
|---|---|---|---|---|---|
| 1.1 | H | Cl | CF$_3$ | NO$_2$ | 157–158 |
| 1.2 | H | Cl | CN | NO$_2$ | |
| 1.3 | H | Cl | COOC$_2$H$_5$ | NO$_2$ | |
| 1.4 | H | Cl | CONH$_2$ | NO$_2$ | |
| 1.5 | H | Cl | COOH | NO$_2$ | |
| 1.6 | H | F | CF$_3$ | NO$_2$ | |
| 1.7 | H | OCH$_3$ | CF$_3$ | NO$_2$ | |
| 1.8 | H | H | CF$_3$ | NO$_2$ | |
| 1.9 | H | H | CN | NO$_2$ | |
| 1.10 | H | H | Cl | NO$_2$ | |
| 1.11 | H | Cl | Cl | NO$_2$ | |
| 1.12 | H | H | SO$_2$CH$_3$ | NO$_2$ | |
| 1.13 | H | H | COOCH$_3$ | NO$_2$ | |
| 1.14 | H | H | CH$_3$ | NO$_2$ | |
| 1.15 | H | H | NO$_2$ | CF$_3$ | 112–115 |
| 1.16 | H | H | NO$_2$ | Cl | |
| 1.17 | H | H | NO$_2$ | CH$_3$CHC$_2$H$_5$ | |
| 1.18 | H | Cl | Cl | Cl | |
| 1.19 | 5-Cl | Cl | CF$_3$ | NO$_2$ | 155–156 |
| 1.20 | 5-Cl | F | CF$_3$ | NO$_2$ | |
| 1.21 | 5-Cl | Br | CF$_3$ | NO$_2$ | |
| 1.22 | 5-Cl | CF$_3$ | CF$_3$ | NO$_2$ | |
| 1.23 | 5-Cl | OCH$_3$ | CF$_3$ | NO$_2$ | |
| 1.24 | 5-Cl | OC$_2$H$_5$ | CF$_3$ | NO$_2$ | |
| 1.25 | 5-Cl | OC$_4$H$_9^{(n)}$ | CF$_3$ | NO$_2$ | |
| 1.26 | 5-Cl | OCF$_3$ | CF$_3$ | NO$_2$ | |
| 1.27 | 5-Cl | OCF$_2$CHF$_2$ | CF$_3$ | NO$_2$ | |
| 1.28 | 5-Cl | OC$_6$H$_5$ | CF$_3$ | NO$_2$ | |
| 1.29 | 5-Cl | SC$_6$H$_5$ | CF$_3$ | NO$_2$ | |
| 1.30 | 5-Cl | OC$_6$H$_4$-p-Cl | CF$_3$ | NO$_2$ | |
| 1.31 | 5-Cl | SC$_6$H$_4$-p-Cl | CF$_3$ | NO$_2$ | |
| 1.32 | 5-Cl | H | CF$_3$ | NO$_2$ | 167–168 |
| 1.33 | 5-Cl | H | H | Cl | |
| 1.34 | 5-Cl | H | Br | NO$_2$ | |
| 1.35 | 5-Cl | H | Cl | NO$_2$ | |
| 1.36 | 5-Cl | H | CONH$_2$ | NO$_2$ | |
| 1.37 | 5-Cl | H | CONH$_2$ | NO$_2$ | |
| 1.38 | 5-Cl | H | COOH | NO$_2$ | |
| 1.39 | 5-Cl | H | COOH | NO$_2$ | |
| 1.40 | 5-Cl | H | COOCH$_3$ | NO$_2$ | |
| 1.41 | 5-Cl | Cl | CN | NO$_2$ | |
| 1.42 | 5-Cl | Cl | COOC$_2$H$_5$ | NO$_2$ | 216–220 |
| 1.43 | 5-Cl | Cl | CONH$_2$ | NO$_2$ | |
| 1.44 | 5-Cl | Cl | COOH | NO$_2$ | |
| 1.45 | 5-Cl | H | SO$_2$CH$_3$ | NO$_2$ | |
| 1.46 | 5-Cl | H | SO$_2$NH$_2$ | NO$_2$ | |
| 1.47 | 5-Cl | H | SO$_2$N(CH$_3$)$_2$ | NO$_2$ | |
| 1.48 | 5-Cl | H | CH$_3$ | NO$_2$ | |
| 1.49 | 5-Cl | H | C(CH$_3$)$_3$ | NO$_2$ | |
| 1.50 | 5-Cl | H | OCF$_3$ | NO$_2$ | |
| 1.51 | 5-Cl | H | OCF$_2$CHF$_2$ | NO$_2$ | |
| 1.52 | 5-Cl | H | NO$_2$ | CF$_3$ | 153–155 |

TABLE 1-continued

3-Cyanopyridine derivatives

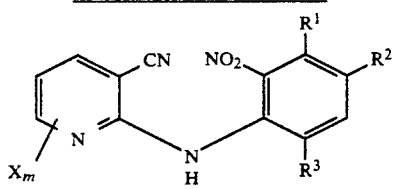

| No. | $X_m$ | $R^1$ | $R^2$ | $R^3$ | m.p. (°C.) |
|---|---|---|---|---|---|
| 1.53 | 5-Cl | H | $NO_2$ | Cl | 212–213 |
| 1.54 | 5-Cl | H | $NO_2$ | $CH_3$ | |
| 1.55 | 5-Cl | H | $NO_2$ | $CH_3$<br>$\|$<br>$CHC_2H_5$ | |
| 1.56 | 5-Cl | Cl | Cl | $NO_2$ | |
| 1.57 | 5-Cl | Cl | Cl | Cl | |
| 1.58 | 5-Cl | H | $CF_3$ | H | |
| 1.59 | 5-Cl | Cl | H | H | |
| 1.60 | 5-$CH_3$ | Cl | $CF_3$ | $NO_2$ | |
| 1.61 | 5-$CH_3$ | F | $CF_3$ | $NO_2$ | |
| 1.62 | 5-$CH_3$ | H | $CF_3$ | $NO_2$ | |
| 1.63 | 5-$CH_3$ | H | $NO_2$ | $CF_3$ | |
| 1.64 | 5-$CH_3$ | H | $NO_2$ | Cl | |
| 1.65 | 5-$CH_3$ | Cl | Cl | $NO_2$ | |
| 1.66 | 5-$CH_3$ | Cl | CN | $NO_2$ | |
| 1.67 | 5-$CH_3$ | Cl | $COOC_2H_5$ | $NO_2$ | |
| 1.68 | 5-Br | Cl | $CF_3$ | $NO_2$ | 136–138 |
| 1.69 | 5-Br | Cl | CN | $NO_2$ | |
| 1.70 | 5-Br | Cl | $COOC_2H_5$ | $NO_2$ | |
| 1.71 | 5-Br | Cl | $CONH_2$ | $NO_2$ | |
| 1.72 | 5-Br | F | $CF_3$ | $NO_2$ | |
| 1.73 | 5-Br | $OCH_3$ | $CF_3$ | $NO_2$ | |
| 1.74 | 5-Br | H | $CF_3$ | $NO_2$ | |
| 1.75 | 5-Br | H | CN | $NO_2$ | |
| 1.76 | 5-Br | H | Cl | $NO_2$ | |
| 1.77 | 5-Br | Cl | Cl | $NO_2$ | |
| 1.78 | 5-Br | H | $SO_2CH_3$ | $NO_2$ | |
| 1.79 | 5-Br | H | $COOCH_3$ | $NO_2$ | |
| 1.80 | 5-Br | H | $CH_3$ | $NO_2$ | |
| 1.81 | 5-Br | H | $NO_2$ | $CF_3$ | 154–156 |
| 1.82 | 5-Br | H | $NO_2$ | Cl | |
| 1.83 | 5-Br | H | $NO_2$ | $CH_3$<br>$\|$<br>$CH-C_2H_5$ | |
| 1.84 | 5-Br | Cl | Cl | Cl | |
| 1.85 | 5-$CF_3$ | Cl | $CF_3$ | $NO_2$ | |
| 1.86 | 5-$CF_3$ | F | $CF_3$ | $NO_2$ | |
| 1.87 | 5-$CF_3$ | H | $CF_3$ | $NO_2$ | |
| 1.88 | 5-$CF_3$ | H | $NO_2$ | $CF_3$ | |
| 1.89 | 5-$CF_3$ | H | $NO_2$ | Cl | |
| 1.90 | 5-$CF_3$ | Cl | Cl | $NO_2$ | |
| 1.91 | 5-$CF_3$ | Cl | CN | $NO_2$ | |
| 1.92 | 5-$CF_3$ | Cl | $COOC_2H_5$ | $NO_2$ | |
| 1.93 | 6-Cl | Cl | $CF_3$ | $NO_2$ | 130–134 |
| 1.94 | 6-Cl | F | $CF_3$ | $NO_2$ | |
| 1.95 | 6-Cl | Br | $CF_3$ | $NO_2$ | |
| 1.96 | 6-Cl | $CF_3$ | $CF_3$ | $NO_2$ | |
| 1.97 | 6-Cl | $OCH_3$ | $CF_3$ | $NO_2$ | |
| 1.98 | 6-Cl | $OC_2H_5$ | $CF_3$ | $NO_2$ | |
| 1.99 | 6-Cl | O-n-$C_4H_9$ | $CF_3$ | $NO_2$ | |
| 1.100 | 6-Cl | $OCF_3$ | $CF_3$ | $NO_2$ | |
| 1.101 | 6-Cl | $OCF_2CHF_2$ | $CF_3$ | $NO_2$ | |
| 1.102 | 6-Cl | $OC_6H_5$ | $CF_3$ | $NO_2$ | |
| 1.103 | 6-Cl | $SC_6H_5$ | $CF_3$ | $NO_2$ | |
| 1.104 | 6-Cl | $OC_6H_4$-p-Cl | $CF_3$ | $NO_2$ | |
| 1.105 | 6-Cl | $SC_6H_4$-p-Cl | $CF_3$ | $NO_2$ | |
| 1.106 | 6-Cl | H | $CF_3$ | $NO_2$ | |
| 1.107 | 6-Cl | H | H | Cl | |
| 1.108 | 6-Cl | H | Br | $NO_2$ | |
| 1.109 | 6-Cl | H | Cl | $NO_2$ | |
| 1.110 | 6-Cl | H | CN | $NO_2$ | |
| 1.111 | 6-Cl | H | $CONH_2$ | $NO_2$ | |
| 1.112 | 6-Cl | H | $CON(CH_3)_2$ | $NO_2$ | |
| 1.113 | 6-Cl | H | COOH | $NO_2$ | |
| 1.114 | 6-Cl | H | $COOCH_3$ | $NO_2$ | |

TABLE 1-continued

3-Cyanopyridine derivatives

| No. | $X_m$ | $R^1$ | $R^2$ | $R^3$ | m.p. (°C.) |
|---|---|---|---|---|---|
| 1.115 | 6-Cl | Cl | CN | NO$_2$ | |
| 1.116 | 6-Cl | Cl | COOC$_2$H$_5$ | NO$_2$ | |
| 1.117 | 6-Cl | Cl | CONH$_2$ | NO$_2$ | |
| 1.118 | 6-Cl | Cl | COOH | NO$_2$ | |
| 1.119 | 6-Cl | H | SO$_2$CH$_3$ | NO$_2$ | |
| 1.120 | 6-Cl | H | SO$_2$NH$_2$ | NO$_2$ | |
| 1.121 | 6-Cl | H | SO$_2$N(CH$_3$)$_2$ | NO$_2$ | |
| 1.122 | 6-Cl | H | CH$_3$ | NO$_2$ | |
| 1.123 | 6-Cl | H | C(CH$_3$)$_3$ | NO$_2$ | |
| 1.124 | 6-Cl | H | OCF$_3$ | NO$_2$ | |
| 1.125 | 6-Cl | H | OCF$_2$CHF$_2$ | NO$_2$ | |
| 1.126 | 6-Cl | H | NO$_2$ | CF$_3$ | 156–159 |
| 1.127 | 6-Cl | H | NO$_2$ | Cl | |
| 1.128 | 6-Cl | H | NO$_2$ | CH$_3$ | |
| 1.129 | 6-Cl | H | NO$_2$ | CH$_3$<br>\|<br>CH—C$_2$H$_5$ | |
| 1.130 | 6-Cl | Cl | Cl | NO$_2$ | |
| 1.131 | 6-Cl | Cl | Cl | Cl | |
| 1.132 | 6-Cl | H | CF$_3$ | H | |
| 1.133 | 6-Br | Cl | CF$_3$ | NO$_2$ | |
| 1.134 | 6-Br | F | CF$_3$ | NO$_2$ | |
| 1.135 | 6-Br | H | CF$_3$ | NO$_2$ | |
| 1.136 | 6-Br | H | NO$_2$ | CF$_3$ | |
| 1.137 | 6-Br | H | NO$_2$ | Cl | |
| 1.138 | 6-Br | Cl | Cl | NO$_2$ | |
| 1.139 | 6-Br | Cl | CN | NO$_2$ | |
| 1.140 | 6-Br | Cl | COOC$_2$H$_5$ | NO$_2$ | |
| 1.141 | 6-cyclo-C$_3$H$_5$ | Cl | CF$_3$ | NO$_2$ | 160 |
| 1.142 | 6-cyclo-C$_3$H$_5$ | F | CF$_3$ | NO$_2$ | |
| 1.143 | 6-cyclo-C$_3$H$_5$ | H | CF$_3$ | NO$_2$ | 168–171 |
| 1.144 | 6-cyclo-C$_3$H$_5$ | H | NO$_2$ | CF$_3$ | 169–173 |
| 1.145 | 6-cyclo-C$_3$H$_5$ | H | NO$_2$ | Cl | |
| 1.146 | 6-cyclo-C$_2$H$_5$ | Cl | Cl | NO$_2$ | |
| 1.147 | 6-cyclo-C$_3$H$_5$ | Cl | CN | NO$_2$ | |
| 1.148 | 6-cyclo-C$_3$H$_5$ | Cl | COOC$_2$H$_5$ | NO$_2$ | |
| 1.149 | 6-CH(CH$_3$)$_2$ | Cl | CF$_3$ | NO$_2$ | 138–141 |
| 1.150 | 6-CH(CH$_3$)$_2$ | F | CF$_3$ | NO$_2$ | |
| 1.151 | 6-CH(CH$_3$)$_2$ | H | CF$_3$ | NO$_2$ | 136 |
| 1.152 | 6-CH(CH$_3$)$_2$ | H | NO$_2$ | CF$_3$ | 125–131 |
| 1.153 | 6-CH(CH$_3$)$_2$ | H | NO$_2$ | Cl | |
| 1.154 | 6-CH(CH$_3$)$_2$ | Cl | Cl | NO$_2$ | |
| 1.155 | 6-CH(CH$_3$)$_2$ | Cl | CN | NO$_2$ | |
| 1.156 | 6-CH(CH$_3$)$_2$ | Cl | COOC$_2$H$_5$ | NO$_2$ | |
| 1.157 | 6-CH$_3$ | Cl | CF$_3$ | NO$_2$ | 163 |
| 1.158 | 6-CH$_3$ | F | CF$_3$ | NO$_2$ | |
| 1.159 | 6-CH$_3$ | H | CF$_3$ | NO$_2$ | 204–206 |
| 1.160 | 6-CH$_3$ | H | NO$_2$ | CF$_3$ | 131–132 |
| 1.161 | 6-CH$_3$ | H | NO$_2$ | Cl | |
| 1.162 | 6-CH$_3$ | Cl | Cl | NO$_2$ | |
| 1.163 | 6-CH$_3$ | Cl | CN | NO$_2$ | |
| 1.164 | 6-CH$_3$ | Cl | COOC$_2$H$_5$ | NO$_2$ | |
| 1.165 | 6-CN | Cl | CF$_3$ | NO$_2$ | |
| 1.166 | 6-CN | F | CF$_3$ | NO$_2$ | |
| 1.167 | 6-CN | H | CF$_3$ | NO$_2$ | |
| 1.168 | 6-CN | H | NO$_2$ | CF$_3$ | |
| 1.169 | 6-CN | H | NO$_2$ | Cl | |
| 1.170 | 6-CN | Cl | Cl | NO$_2$ | |
| 1.171 | 6-CN | Cl | CN | NO$_2$ | |
| 1.172 | 6-CN | Cl | COOC$_2$H$_5$ | NO$_2$ | |
| 1.173 | 6-SC$_6$H$_5$ | Cl | CF$_3$ | NO$_2$ | |
| 1.174 | 6-SC$_6$H$_5$ | F | CF$_3$ | NO$_2$ | |
| 1.175 | 6-SC$_6$H$_5$ | H | CF$_3$ | NO$_2$ | |
| 1.176 | 6-SC$_6$H$_5$ | H | NO$_2$ | CF$_3$ | |
| 1.177 | 6-SC$_6$H$_5$ | H | NO$_2$ | Cl | |
| 1.178 | 6-SC$_6$H$_5$ | Cl | Cl | NO$_2$ | |
| 1.179 | 6-SC$_6$H$_5$ | Cl | CN | NO$_2$ | |
| 1.180 | 6-SC$_6$H$_5$ | Cl | COOC$_2$H$_5$ | NO$_2$ | |

TABLE 1-continued

3-Cyanopyridine derivatives

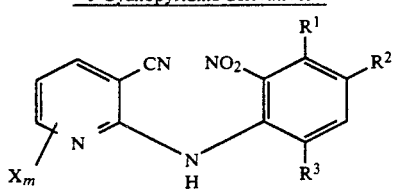

| No. | $X_m$ | $R^1$ | $R^2$ | $R^3$ | m.p. (°C.) |
|---|---|---|---|---|---|
| 1.181 | 6-SC$_6$H$_5$ | Cl | CF$_3$ | NO$_2$ | |
| 1.182 | 6-SC$_6$H$_5$ | F | CF$_3$ | NO$_2$ | |
| 1.183 | 6-SC$_6$H$_5$ | H | CF$_3$ | NO$_2$ | |
| 1.184 | 6-SC$_6$H$_5$ | H | NO$_2$ | CF$_3$ | |
| 1.185 | 6-SC$_6$H$_5$ | H | NO$_2$ | Cl | |
| 1.186 | 6-SC$_6$H$_5$ | Cl | Cl | NO$_2$ | |
| 1.187 | 6-SC$_6$H$_5$ | Cl | CN | NO$_2$ | |
| 1.188 | 6-SC$_6$H$_5$ | Cl | COOC$_2$H$_5$ | NO$_2$ | |
| 1.189 | 6-OC$_2$H$_5$ | Cl | CF$_3$ | NO$_2$ | |
| 1.190 | 6-OC$_2$H$_5$ | F | CF$_3$ | NO$_2$ | |
| 1.191 | 6-OC$_2$H$_5$ | H | CF$_3$ | NO$_2$ | |
| 1.192 | 6-OC$_2$H$_5$ | H | NO$_2$ | CF$_3$ | |
| 1.193 | 6-OC$_2$H$_5$ | H | NO$_2$ | Cl | |
| 1.194 | 6-OC$_2$H$_5$ | Cl | Cl | NO$_2$ | |
| 1.195 | 6-OC$_2$H$_5$ | Cl | CN | NO$_2$ | |
| 1.196 | 6-OC$_2$H$_5$ | Cl | COOC$_2$H$_5$ | NO$_2$ | |
| 1.197 | 4,6-(CH$_3$)$_2$ | Cl | CF$_3$ | NO$_2$ | 165 |
| 1.198 | 4,6-(CH$_3$)$_2$ | F | CF$_3$ | NO$_2$ | |
| 1.199 | 4,6-(CH$_3$)$_2$ | H | CF$_3$ | NO$_2$ | 215–216 |
| 1.200 | 4,6-(CH$_3$)$_2$ | H | NO$_2$ | CF$_3$ | 145–152 |
| 1.201 | 4,6-(CH$_3$)$_2$ | H | NO$_2$ | Cl | |
| 1.202 | 4,6-(CH$_3$)$_2$ | H | C(CH$_3$)$_3$ | NO$_2$ | 192–194 |
| 1.203 | 4,6-(CH$_3$)$_2$ | Cl | Cl | NO$_2$ | |
| 1.204 | 4,6-(CH$_3$)$_2$ | Cl | CN | NO$_2$ | |
| 1.205 | 4,6-(CH$_3$)$_2$ | H | CN | NO$_2$ | 203 decomp. |
| 1.206 | 4,6-(CH$_3$)$_2$ | Cl | COOC$_2$H$_5$ | NO$_2$ | |
| 1.207 | 4-CH$_3$, 6-Cl | Cl | CF$_3$ | NO$_2$ | 148–158 |
| 1.208 | 4-CH$_3$, 6-Cl | F | CF$_3$ | NO$_2$ | |
| 1.209 | 4-CH$_3$, 6-Cl | H | CF$_3$ | NO$_2$ | |
| 1.210 | 4-CH$_3$, 6-Cl | H | NO$_2$ | CF$_3$ | 128–133 |
| 1.211 | 4-CH$_3$, 6-Cl | H | NO$_2$ | Cl | |
| 1.212 | 4-CH$_3$, 6-Cl | Cl | Cl | NO$_2$ | |
| 1.213 | 4-CH$_3$, 6-Cl | Cl | CN | NO$_2$ | |
| 1.214 | 4-CH$_3$, 6-Cl | Cl | COOC$_2$H$_5$ | NO$_2$ | |
| 1.215 | 5-CN | Cl | CF$_3$ | NO$_2$ | |
| 1.216 | 5-CN | F | CF$_3$ | NO$_2$ | |
| 1.217 | 5-CN | H | CF$_3$ | NO$_2$ | |
| 1.218 | 5-CN | H | NO$_2$ | CF$_3$ | |
| 1.219 | 5-CN | H | NO$_2$ | Cl | |
| 1.220 | 5-CN | Cl | Cl | NO$_2$ | |
| 1.221 | 5-CN | Cl | CN | NO$_2$ | |
| 1.222 | 5-CN | Cl | COOC$_2$H$_5$ | NO$_2$ | |
| 1.223 | 5-CN, 6-CH$_3$ | Cl | CF$_3$ | NO$_2$ | >220 |
| 1.224 | 5-CN, 6-CH$_3$ | F | CF$_3$ | NO$_2$ | |
| 1.225 | 5-CN, 6-CH$_3$ | H | CF$_3$ | NO$_2$ | |
| 1.226 | 5-CN, 6-CH$_3$ | H | NO$_2$ | CF$_3$ | 125 |
| 1.227 | 5-CN, 6-CH$_3$ | H | NO$_2$ | Cl | |
| 1.228 | 5-CN, 6-CH$_3$ | Cl | Cl | NO$_2$ | |
| 1.229 | 5-CN, 6-CH$_3$ | Cl | CN | NO$_2$ | |
| 1.230 | 5-CN, 6-CH$_3$ | Cl | COOC$_2$H$_5$ | NO$_2$ | |
| 1.231 | 4-CH$_3$, 5-CN, 6-OC$_2$H$_5$ | Cl | CF$_3$ | NO$_2$ | 120 |
| 1.232 | 4-CH$_3$, 5-CN, 6-OC$_2$H$_5$ | F | CF$_3$ | NO$_2$ | |
| 1.233 | 4-CH$_3$, 5-CN, 6-OC$_2$H$_5$ | H | CF$_3$ | NO$_2$ | |
| 1.234 | 4-CH$_3$, 5-CN, 6-OC$_2$H$_5$ | H | NO$_2$ | CF$_3$ | >220 |
| 1.235 | 4-CH$_3$, 5-CN, 6-OC$_2$H$_5$ | H | NO$_2$ | Cl | |
| 1.236 | 4-CH$_3$, 5-CN, 6-OC$_2$H$_5$ | Cl | CN | NO$_2$ | |
| 1.237 | 4-CH$_3$, 5-CN, 6-OC$_2$H$_5$ | Cl | CN | NO$_2$ | |
| 1.238 | 4-CH$_3$, 5-CN, 6-OC$_2$H$_5$ | Cl | COOC$_2$H$_5$ | NO$_2$ | |
| 1.239 | 4-CH(CH$_3$)$_2$, 5-CN, 6-OC$_2$H$_5$ | Cl | CF$_3$ | NO$_2$ | 165–167 |
| 1.240 | 4-CH(CH$_3$)$_2$, 5-CN, 6-OC$_2$H$_5$ | Cl | CN | NO$_2$ | |
| 1.241 | 4-CH(CH$_3$)$_2$, 5-CN, 6-OC$_2$H$_5$ | Cl | COOC$_2$H$_5$ | NO$_2$ | 173–174 |
| 1.242 | 4-CH(CH$_3$)$_2$, 5-CN, 6-OC$_2$H$_5$ | Cl | CONH$_2$ | NO$_2$ | |
| 1.243 | 4-CH(CH$_3$)$_2$, 5-CN, 6-OC$_2$H$_5$ | Cl | COOH | NO$_2$ | |
| 1.244 | 4-CH(CH$_3$)$_2$, 5-CN, 6-OC$_2$H$_5$ | F | CF$_3$ | NO$_2$ | |
| 1.245 | 4-CH(CH$_3$)$_2$, 5-CN, 6-OC$_2$H$_5$ | OCH$_3$ | CF$_3$ | NO$_2$ | |
| 1.246 | 4-CH(CH$_3$)$_2$, 5-CN, 6-OC$_2$H$_5$ | H | CF$_3$ | NO$_2$ | |
| 1.247 | 4-CH(CH$_3$)$_2$, 5-CN, 6-OC$_2$H$_5$ | H | CN | NO$_2$ | |
| 1.248 | 4-CH(CH$_3$)$_2$, 5-CN, 6-OC$_2$H$_5$ | H | Cl | NO$_2$ | |
| 1.249 | 4-CH(CH$_3$)$_2$, 5-CN, 6-OC$_2$H$_5$ | Cl | Cl | NO$_2$ | 167 |
| 1.250 | 4-CH(CH$_3$)$_2$, 5-CN, 6-OC$_2$H$_5$ | H | SO$_2$CH$_3$ | NO$_2$ | |

TABLE 1-continued
3-Cyanopyridine derivatives

| No. | $X_m$ | $R^1$ | $R^2$ | $R^3$ | m.p. (°C.) |
|---|---|---|---|---|---|
| 1.251 | 4-CH(CH$_3$)$_2$, 5-CN, 6-OC$_2$H$_5$ | H | COOCH$_3$ | NO$_2$ | |
| 1.252 | 4-CH(CH$_3$)$_2$, 5-CN, 6-OC$_2$H$_5$ | H | CH$_3$ | NO$_2$ | |
| 1.253 | 4-CH(CH$_3$)$_2$, 5-CN, 6-OC$_2$H$_5$ | H | NO$_2$ | CF$_3$ | 183–185 |
| 1.254 | 4-CH(CH$_3$)$_2$, 5-CN, 6-OC$_2$H$_5$ | H | NO$_2$ | Cl | 219–221 |
| 1.255 | 4-CH(CH$_3$)$_2$, 5-CN, 6-OC$_2$H$_5$ | H | NO$_2$ | CH(CH$_3$)—C$_2$H$_5$ | |
| 1.256 | 4-CH(CH$_3$)$_2$, 5-CN, 6-OC$_2$H$_5$ | Cl | Cl | Cl | |
| 1.257 | 5-NO$_2$ | Cl | CF$_3$ | NO$_2$ | |
| 1.258 | 5-NO$_2$ | F | CF$_3$ | NO$_2$ | |
| 1.259 | 5-NO$_2$ | H | CF$_3$ | NO$_2$ | |
| 1.260 | 5-NO$_2$ | H | NO$_2$ | CF$_3$ | |
| 1.261 | 5-NO$_2$ | H | NO$_2$ | Cl | |
| 1.262 | 5-NO$_2$ | Cl | Cl | NO$_2$ | |
| 1.263 | 5-NO$_2$ | Cl | CN | NO$_2$ | |
| 1.264 | 5-NO$_2$ | Cl | COOC$_2$H$_5$ | NO$_2$ | |
| 1.265 | 6-SO$_2$CH$_3$ | Cl | CF$_3$ | NO$_2$ | |
| 1.266 | 6-SO$_2$CH$_3$ | H | NO$_2$ | CF$_3$ | |
| 1.267 | 6-OCH$_3$ | Cl | CF$_3$ | NO$_2$ | |
| 12.68 | 6-OCH$_3$ | H | NO$_2$ | CF$_3$ | |
| 1.269 | 4-CH$_3$, 5-CN, 6-OCH$_3$ | Cl | CF$_3$ | NO$_2$ | |
| 1.270 | 4-CH$_3$, 5-CN, 6-OCH$_3$ | H | NO$_2$ | CF$_3$ | |
| 1.271 | 4-CH(CH$_3$)$_2$, 5-CN, 6-OCH$_3$ | Cl | CF$_3$ | NO$_2$ | |
| 1.272 | 4-CH(CH$_3$)$_2$, 5-CN, 6-OCH$_3$ | H | NO$_2$ | CF$_3$ | |
| 1.273 | 4-C$_2$H$_5$, 5-CN, 6-OC$_2$H$_5$ | Cl | CF$_3$ | NO$_2$ | |
| 1.274 | 4-C$_2$H$_5$, 5-CN, 6-OC$_2$H$_5$ | H | NO$_2$ | CF$_3$ | |
| 1.275 | 4-CH$_3$, 6-Br | Cl | CF$_3$ | NO$_2$ | |
| 1.276 | 4-CH$_3$, 6-Br | H | NO$_2$ | CF$_3$ | |
| 1.277 | 6-cyclo-C$_6$H$_9$ | Cl | CF$_3$ | NO$_2$ | |
| 1.278 | 6-cyclo-C$_5$H$_9$ | H | NO$_2$ | CF$_3$ | |
| 1.279 | 4-cyclo-C$_3$H$_5$, 6-Cl | Cl | CF$_3$ | NO$_2$ | |
| 1.280 | 4-cyclo-C$_3$H$_5$, 6-Cl | H | NO$_2$ | CF$_3$ | |
| 1.281 | 5-CN, 6-cyclo-C$_3$H$_5$ | Cl | CF$_3$ | NO$_2$ | |
| 1.282 | 5-CN, 6-cyclo-C$_3$H$_5$ | H | NO$_2$ | CF$_3$ | |
| 1.283 | 6-OPh-4-Cl | Cl | CF$_3$ | NO$_2$ | |
| 1.284 | 6-OPh-4-Cl | H | NO$_2$ | CF$_3$ | |
| 1.285 | 6-OPh-4-CH$_3$ | Cl | CF$_3$ | NO$_2$ | |
| 1.286 | 6-OPh-4-CH$_3$ | H | NO$_2$ | CF$_3$ | |
| 1.287 | 6-SPh-4-CH$_3$ | Cl | CF$_3$ | NO$_2$ | |
| 1.288 | 6-SPh-4-CH$_3$ | H | NO$_2$ | CF$_3$ | |

TABLE 2
4-Cyanopyridine derivatives

| No. | $X_m$ | $R^1$ | $R^2$ | $R^3$ | m.p. (°C.) |
|---|---|---|---|---|---|
| 2.1 | 6-Cl | Cl | CF$_3$ | NO$_2$ | |
| 2.2 | 6-Cl | Cl | CN | NO$_2$ | |
| 2.3 | 6-Cl | Cl | COOC$_2$H$_5$ | NO$_2$ | |
| 2.4 | 6-Cl | Cl | CONH$_2$ | NO$_2$ | |
| 2.5 | 6-Cl | Cl | COOH | NO$_2$ | |
| 2.6 | 6-Cl | F | CF$_3$ | NO$_2$ | |
| 2.7 | 6-Cl | OCH$_3$ | CF$_3$ | NO$_2$ | |
| 2.8 | 6-Cl | H | CF$_3$ | NO$_2$ | |
| 2.9 | 6-Cl | H | CN | NO$_2$ | |
| 2.10 | 6-Cl | H | Cl | NO$_2$ | |
| 2.11 | 6-Cl | Cl | Cl | NO$_2$ | |
| 2.12 | 6-Cl | H | SO$_2$CH$_3$ | NO$_2$ | |
| 2.13 | 6-Cl | H | COOCH$_3$ | NO$_2$ | |
| 2.14 | 6-Cl | H | CH$_3$ | NO$_2$ | |
| 2.15 | 6-Cl | H | NO$_2$ | CF$_3$ | |
| 2.16 | 6-Cl | H | NO$_2$ | Cl | |
| 2.17 | 6-Cl | H | NO$_2$ | CH(CH$_3$)—C$_2$H$_5$ | |
| 2.18 | 6-Cl | Cl | Cl | Cl | |
| 2.19 | 6-OC$_2$H$_5$ | Cl | CF$_3$ | NO$_2$ | |
| 2.20 | 6-OC$_2$H$_5$ | F | CF$_3$ | NO$_2$ | |

TABLE 2-continued
4-Cyanopyridine derivatives

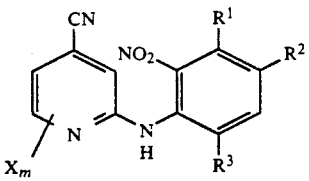

| No. | $X_m$ | $R^1$ | $R^2$ | $R^3$ | m.p. (°C.) |
|---|---|---|---|---|---|
| 2.21 | 6-OC$_2$H$_5$ | H | CF$_3$ | NO$_2$ | |
| 2.22 | 6-OC$_2$H$_5$ | H | NO$_2$ | CF$_3$ | |
| 2.23 | 6-OC$_2$H$_5$ | H | NO$_2$ | Cl | |
| 2.24 | 6-OC$_2$H$_5$ | Cl | Cl | NO$_2$ | |
| 2.25 | 6-OC$_2$H$_5$ | Cl | CN | NO$_2$ | |
| 2.26 | 6-OC$_2$H$_5$ | Cl | COOC$_2$H$_5$ | NO$_2$ | |
| 2.27 | H | Cl | CF$_3$ | NO$_2$ | |
| 2.28 | H | F | CF$_3$ | NO$_2$ | |
| 2.29 | H | H | CF$_3$ | NO$_2$ | |
| 2.30 | H | H | NO$_2$ | CF$_3$ | |
| 2.31 | H | H | NO$_2$ | Cl | |
| 2.32 | H | Cl | Cl | NO$_2$ | |
| 2.33 | H | Cl | CN | NO$_2$ | |
| 2.34 | H | Cl | COOC$_2$H$_5$ | NO$_2$ | |
| 2.35 | 6-OC$_6$H$_5$ | Cl | CF$_3$ | NO$_2$ | |
| 2.36 | 6-OC$_6$H$_5$ | F | CF$_3$ | NO$_2$ | |

TABLE 2-continued
4-Cyanopyridine derivatives

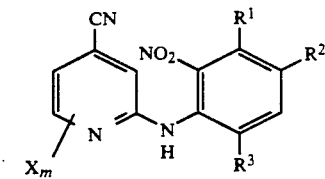

| No. | $X_m$ | $R^1$ | $R^2$ | $R^3$ | m.p. (°C.) |
|---|---|---|---|---|---|
| 2.37 | 6-OC$_6$H$_5$ | H | CF$_3$ | NO$_2$ | |
| 2.38 | 6-OC$_6$H$_5$ | H | NO$_2$ | CF$_3$ | |
| 2.39 | 6-OC$_6$H$_5$ | H | NO$_2$ | Cl | |
| 2.40 | 6-OC$_6$H$_5$ | Cl | Cl | NO$_2$ | |
| 2.41 | 6-OC$_6$H$_5$ | Cl | CN | NO$_2$ | |
| 2.42 | 6-OC$_6$H$_5$ | Cl | COOC$_2$H$_5$ | NO$_2$ | |
| 2.43 | 6-Br | Cl | CF$_3$ | NO$_2$ | |
| 2.44 | 6-Br | H | NO$_2$ | CF$_3$ | |
| 2.45 | 6-F | Cl | CF$_3$ | NO$_2$ | |
| 2.46 | 6-F | H | NO$_2$ | CF$_3$ | |
| 2.47 | 6-SC$_6$H$_5$ | Cl | CF$_3$ | NO$_2$ | |
| 2.48 | 6-SC$_6$H$_5$ | H | NO$_2$ | CF$_3$ | |
| 2.49 | 6-SO$_2$CH$_3$ | Cl | CF$_3$ | NO$_2$ | |
| 2.50 | 6-SO$_2$CH$_3$ | H | NO$_2$ | CF$_3$ | |
| 2.51 | 6-CN | Cl | CF$_3$ | NO$_2$ | |
| 2.52 | 6-CN | H | NO$_2$ | CF$_3$ | |

TABLE 3
5-Cyanopyridine derivatives

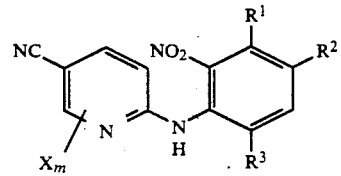

| No. | $X_m$ | $R^1$ | $R^2$ | $R^3$ | m.p. (°C.) |
|---|---|---|---|---|---|
| 3.1 | H | Cl | CF$_3$ | NO$_2$ | 159–161 |
| 3.2 | H | Cl | CN | NO$_2$ | |
| 3.3 | H | Cl | COOC$_2$H$_5$ | NO$_2$ | |
| 3.4 | H | Cl | CONH$_2$ | NO$_2$ | |
| 3.5 | H | Cl | COOH | NO$_2$ | |
| 3.6 | H | F | CF$_3$ | NO$_2$ | |
| 3.7 | H | OCH$_3$ | CF$_3$ | NO$_2$ | |
| 3.8 | H | H | CF$_3$ | NO$_2$ | |
| 3.9 | H | H | CN | NO$_2$ | |
| 3.10 | H | H | Cl | NO$_2$ | |
| 3.11 | H | Cl | Cl | NO$_2$ | |
| 3.12 | H | H | SO$_2$CH$_3$ | NO$_2$ | |
| 3.13 | H | H | COOCH$_3$ | NO$_2$ | |
| 3.14 | H | H | CH$_3$ | NO$_2$ | |
| 3.15 | H | H | NO$_2$ | CF$_3$ | 141–144 |
| 3.16 | H | H | NO$_2$ | Cl | |
| 3.17 | H | H | NO$_2$ | CH(CH$_3$)—C$_2$H$_5$ | |
| 3.18 | H | Cl | Cl | Cl | |
| 3.19 | 3-Cl | Cl | CF$_3$ | NO$_2$ | 173–175 |
| 3.20 | 3-Cl | F | CF$_3$ | NO$_2$ | 133–136 |
| 3.21 | 3-Cl | Br | CF$_3$ | NO$_2$ | |
| 3.22 | 3-Cl | CF$_3$ | CF$_3$ | NO$_2$ | |
| 3.23 | 3-Cl | OCH$_3$ | CF$_3$ | NO$_2$ | |
| 3.24 | 3-Cl | OC$_2$H$_5$ | CF$_3$ | NO$_2$ | |
| 3.25 | 3-Cl | O-n-C$_4$H$_9$ | CF$_3$ | NO$_2$ | |
| 3.26 | 3-Cl | OCF$_3$ | CF$_3$ | NO$_2$ | |
| 3.27 | 3-Cl | OCF$_2$CHF$_2$ | CF$_3$ | NO$_2$ | |
| 3.28 | 3-Cl | OC$_6$H$_5$ | CF$_3$ | NO$_2$ | |
| 3.29 | 3-Cl | SC$_6$H$_5$ | CF$_3$ | NO$_2$ | |
| 3.30 | 3-Cl | OC$_6$H$_4$-p-Cl | CF$_3$ | NO$_2$ | |
| 3.31 | 3-Cl | SC$_6$H$_4$-p-Cl | CF$_3$ | NO$_2$ | |
| 3.32 | 3-Cl | H | CF$_3$ | NO$_2$ | 134–135 |
| 3.33 | 3-Cl | H | H | Cl | |

TABLE 3-continued

5-Cyanopyridine derivatives

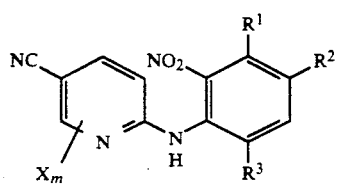

| No. | $X_m$ | $R^1$ | $R^2$ | $R^3$ | m.p. (°C.) |
|---|---|---|---|---|---|
| 3.34 | 3-Cl | H | Br | NO$_2$ | |
| 3.35 | 3-Cl | H | Cl | NO$_2$ | |
| 3.36 | 3-Cl | H | CN | NO$_2$ | 210–212 |
| 3.37 | 3-Cl | H | CONH$_2$ | NO$_2$ | |
| 3.38 | 3-Cl | H | CON(CH$_3$)$_2$ | NO$_2$ | |
| 3.39 | 3-Cl | H | COOH | NO$_2$ | |
| 3.40 | 3-Cl | H | COOCH$_3$ | NO$_2$ | 185–187 |
| 3.41 | 3-Cl | Cl | CN | NO$_2$ | |
| 3.42 | 3-Cl | Cl | COOC$_2$H$_5$ | NO$_2$ | 182–188 |
| 3.43 | 3-Cl | Cl | CONH$_2$ | NO$_2$ | |
| 3.44 | 3-Cl | Cl | COOH | NO$_2$ | |
| 3.45 | 3-Cl | H | SO$_2$CH$_3$ | NO$_2$ | >220 |
| 3.46 | 3-Cl | H | SO$_2$NH$_2$ | NO$_2$ | |
| 3.47 | 3-Cl | H | SO$_2$N(CH$_3$)$_2$ | NO$_2$ | |
| 3.48 | 3-Cl | H | CH$_3$ | NO$_2$ | 155 |
| 3.49 | 3-Cl | H | C(CH$_3$)$_3$ | NO$_2$ | 175–178 |
| 3.50 | 3-Cl | H | OCF$_3$ | NO$_2$ | |
| 3.51 | 3-Cl | H | OCF$_2$CHF$_2$ | NO$_2$ | |
| 3.52 | 3-Cl | H | NO$_2$ | CF$_3$ | 117–119 |
| 3.53 | 3-Cl | H | NO$_2$ | Cl | 135–138 |
| 3.54 | 3-Cl | H | NO$_2$ | CH$_3$ | |
| 3.55 | 3-Cl | H | NO$_2$ | CH$_3$<br>\|<br>CH—C$_2$H$_5$ | 134–138 |
| 3.56 | 3-Cl | Cl | Cl | NO$_2$ | |
| 3.57 | 3-Cl | Cl | Cl | Cl | 157–158 |
| 3.58 | 3-Cl | H | CF$_3$ | H | 164–170 |
| 3.59 | 3-Cl | Cl | H | H | |
| 3.60 | 3-NO$_2$ | Cl | CF$_3$ | NO$_2$ | |
| 3.61 | 3-NO$_2$ | F | CF$_3$ | NO$_2$ | |
| 3.62 | 3-NO$_2$ | H | CF$_3$ | NO$_2$ | |
| 3.63 | 3-NO$_2$ | H | NO$_2$ | CF$_3$ | |
| 3.64 | 3-NO$_2$ | H | NO$_2$ | Cl | |
| 3.65 | 3-NO$_2$ | Cl | Cl | NO$_2$ | |
| 3.66 | 3-NO$_2$ | Cl | CN | NO$_2$ | |
| 3.67 | 3-NO$_2$ | Cl | COOC$_2$H$_5$ | NO$_2$ | |
| 3.68 | 3-Br | Cl | CF$_3$ | NO$_2$ | 151–155 |
| 3.69 | 3-Br | Cl | CN | NO$_2$ | |
| 3.70 | 3-Br | Cl | COOC$_2$H$_5$ | NO$_2$ | |
| 3.71 | 3-Br | Cl | CONH$_2$ | NO$_2$ | |
| 3.72 | 3-Br | F | CF$_3$ | NO$_2$ | |
| 3.73 | 3-Br | OCH$_3$ | CF$_3$ | NO$_2$ | |
| 3.74 | 3-Br | H | CF$_3$ | NO$_2$ | |
| 3.75 | 3-Br | H | CN | NO$_2$ | |
| 3.76 | 3-Br | H | Cl | NO$_2$ | |
| 3.77 | 3-Br | Cl | Cl | NO$_2$ | |
| 3.78 | 3-Br | H | SO$_2$CH$_3$ | NO$_2$ | |
| 3.79 | 3-Br | H | COOCH$_3$ | NO$_2$ | |
| 3.80 | 3-Br | H | CH$_3$ | NO$_2$ | |
| 3.81 | 3-Br | H | NO$_2$ | CF$_3$ | 124–126 |
| 3.82 | 3-Br | H | NO$_2$ | Cl | |
| 3.83 | 3-Br | H | NO$_2$ | CH$_3$<br>\|<br>CH—C$_2$H$_5$ | |
| 3.84 | 3-Br | Cl | Cl | Cl | |
| 3.85 | 3-CF$_3$ | Cl | CF$_3$ | NO$_2$ | |
| 3.86 | 3-CF$_3$ | F | CF$_3$ | NO$_2$ | |
| 3.87 | 3-CF$_3$ | H | CF$_3$ | NO$_2$ | |
| 3.88 | 3-CF$_3$ | H | NO$_2$ | CF$_3$ | |
| 3.89 | 3-CF$_3$ | H | NO$_2$ | Cl | |
| 3.90 | 3-CF$_3$ | Cl | Cl | NO$_2$ | |
| 3.91 | 3-CF$_3$ | Cl | CN | NO$_2$ | |
| 3.92 | 3-CF$_3$ | Cl | COOC$_2$H$_5$ | NO$_2$ | |
| 3.93 | 4,6-(CH$_3$)$_2$ | Cl | CF$_3$ | NO$_2$ | >220 |
| 3.94 | 4,6-(CH$_3$)$_2$ | F | CF$_3$ | NO$_2$ | |

TABLE 3-continued
5-Cyanopyridine derivatives

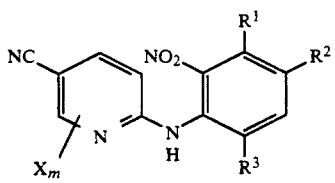

| No. | $X_m$ | $R^1$ | $R^2$ | $R^3$ | m.p. (°C.) |
|---|---|---|---|---|---|
| 3.95 | 4,6-(CH$_3$)$_2$ | H | CF$_3$ | NO$_2$ | |
| 3.96 | 4,6-(CH$_3$)$_2$ | H | NO$_2$ | CF$_3$ | |
| 3.97 | 4,6-(CH$_3$)$_2$ | H | NO$_2$ | Cl | |
| 3.98 | 4,6-(CH$_3$)$_2$ | Cl | Cl | NO$_2$ | |
| 3.99 | 4,6-(CH$_3$)$_2$ | Cl | CN | NO$_2$ | |
| 3.100 | 4,6-(CH$_3$)$_2$ | Cl | COOC$_2$H$_5$ | NO$_2$ | |
| 3.101 | 6-Cl | Cl | CF$_3$ | NO$_2$ | 203–204 |
| 3.102 | 6-Cl | F | CF$_3$ | NO$_2$ | |
| 3.103 | 6-Cl | H | CF$_3$ | NO$_2$ | |
| 3.104 | 6-Cl | H | NO$_2$ | CF$_3$ | 176–185 |
| 3.105 | 6-Cl | H | NO$_2$ | Cl | |
| 3.106 | 6-Cl | Cl | Cl | NO$_2$ | |
| 3.107 | 6-Cl | Cl | CN | NO$_2$ | |
| 3.108 | 6-Cl | Cl | COOC$_2$H$_5$ | NO$_2$ | |
| 3.109 | 3,6-Cl$_2$ | Cl | CF$_3$ | NO$_2$ | |
| 3.110 | 3,6-Cl$_2$ | F | CF$_3$ | NO$_2$ | |
| 3.111 | 3,6-Cl$_2$ | H | CF$_3$ | NO$_2$ | |
| 3.112 | 3,6-Cl$_2$ | H | NO$_2$ | CF$_3$ | |
| 3.113 | 3,6-Cl$_2$ | H | NO$_2$ | Cl | |
| 3.114 | 3,6-Cl$_2$ | Cl | Cl | NO$_2$ | |
| 3.115 | 3,6-Cl$_2$ | Cl | CN | NO$_2$ | |
| 3.116 | 3,6-Cl$_2$ | Cl | COOC$_2$H$_5$ | NO$_2$ | |
| 3.117 | 4-CH$_3$ | Cl | CF$_3$ | NO$_2$ | |
| 3.118 | 4-CH$_3$ | H | NO$_2$ | CF$_3$ | |
| 3.119 | 6-CH$_3$ | Cl | CF$_3$ | NO$_2$ | |
| 3.120 | 6-CH$_3$ | H | NO$_2$ | CF$_3$ | |
| 3.121 | 3-Cl, 6-OC$_2$H$_5$ | Cl | CF$_3$ | NO$_2$ | |
| 3.122 | 3-Cl, 6-OC$_2$H$_5$ | H | NO$_2$ | CF$_3$ | |
| 3.123 | 3-Cl, 6-OC$_6$H$_5$ | Cl | CF$_3$ | NO$_2$ | |
| 3.124 | 3-Cl, 6-OC$_6$H$_5$ | H | NO$_2$ | CF$_3$ | |
| 3.125 | 3-Cl, 6-SO$_2$CH$_3$ | Cl | CF$_3$ | NO$_2$ | |
| 3.126 | 3-Cl, 6-SO$_2$CH$_3$ | H | NO$_2$ | CF$_3$ | |

TABLE 4
6-Cyanopyridine derivatives

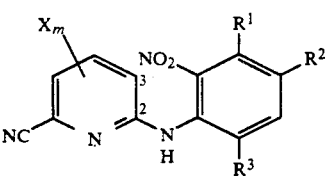

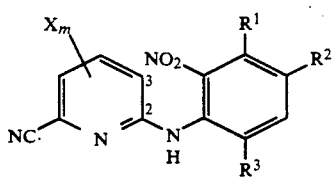

| No. | $X_m$ | $R^1$ | $R^2$ | $R^3$ | m.p. (°C.) |
|---|---|---|---|---|---|
| 4.1 | H | H | Cl | CF$_3$ | NO$_2$ |
| 4.2 | H | F | CF$_3$ | NO$_2$ | |
| 4.3 | H | H | CF$_3$ | NO$_2$ | |
| 4.4 | H | H | NO$_2$ | CF$_3$ | |
| 4.5 | H | H | NO$_2$ | Cl | |
| 4.6 | H | Cl | Cl | NO$_2$ | |
| 4.7 | H | Cl | CN | NO$_2$ | |
| 4.8 | H | Cl | COOC$_2$H$_5$ | NO$_2$ | |
| 4.9 | 3-Cl, 5-CF$_3$ | Cl | CF$_3$ | NO$_2$ | |
| 4.10 | 3-Cl, 5-CF$_3$ | F | CF$_3$ | NO$_2$ | |
| 4.11 | 3-Cl, 5-CF$_3$ | H | CF$_3$ | NO$_2$ | |
| 4.12 | 3-Cl, 5-CF$_3$ | H | NO$_2$ | CF$_3$ | |
| 4.13 | 3-Cl, 5-CF$_3$ | H | NO$_2$ | Cl | |
| 4.14 | 3-Cl, 5-CF$_3$ | Cl | Cl | NO$_2$ | |
| 4.15 | 3-Cl, 5-CF$_3$ | Cl | CN | NO$_2$ | |
| 4.16 | 3-Cl, 5-CF$_3$ | Cl | COOC$_2$H$_5$ | NO$_2$ | |
| 4.17 | 3,5-Cl$_2$ | Cl | CF$_3$ | NO$_2$ | |
| 4.18 | 3,5-Cl$_2$ | F | CF$_3$ | NO$_2$ | |
| 4.19 | 3,5-Cl$_2$ | H | CF$_3$ | NO$_2$ | |
| 4.20 | 3,5-Cl$_2$ | H | NO$_2$ | CF$_3$ | |
| 4.21 | 3,5-Cl$_2$ | H | NO$_2$ | Cl | |
| 4.22 | 3,5-Cl$_2$ | Cl | Cl | NO$_2$ | |
| 4.23 | 3,5-Cl$_2$ | Cl | CN | NO$_2$ | |
| 4.24 | 3,5-Cl$_2$ | Cl | COOC$_2$H$_5$ | NO$_2$ | |
| 4.25 | 3-CF$_3$ | Cl | CF$_3$ | NO$_2$ | |
| 4.26 | 3-CF$_3$ | F | CF$_3$ | NO$_2$ | |
| 4.27 | 3-CF$_3$ | H | CF$_3$ | NO$_2$ | |
| 4.28 | 3-CF$_3$ | H | NO$_2$ | CF$_3$ | |
| 4.29 | 3-CF$_3$ | H | NO$_2$ | Cl | |
| 4.30 | 3-CF$_3$ | Cl | Cl | NO$_2$ | |
| 4.31 | 3-CF$_3$ | Cl | CN | NO$_2$ | |
| 4.32 | 3-CF$_3$ | Cl | COOC$_2$H$_5$ | NO$_2$ | |
| 4.33 | 5-CF$_3$ | Cl | CF$_3$ | NO$_2$ | |
| 4.34 | 5-CF$_3$ | F | CF$_3$ | NO$_2$ | |
| 4.35 | 5-CF$_3$ | H | CF$_3$ | NO$_2$ | |
| 4.36 | 5-CF$_3$ | H | NO$_2$ | CF$_3$ | |
| 4.37 | 5-CF$_3$ | H | NO$_2$ | Cl | |
| 4.38 | 5-CF$_3$ | Cl | Cl | NO$_2$ | |
| 4.39 | 5-CF$_3$ | Cl | CN | NO$_2$ | |
| 4.40 | 5-CF$_3$ | Cl | COOC$_2$H$_5$ | NO$_2$ | |
| 4.41 | 4-CF$_3$ | Cl | CF$_3$ | NO$_2$ | |

TABLE 4-continued

6-Cyanopyridine derivatives

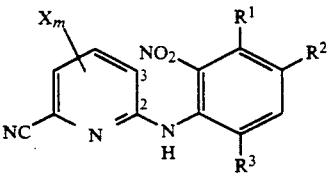

| No. | $X_m$ | $R^1$ | $R^2$ | $R^3$ | m.p. (°C.) |
|---|---|---|---|---|---|
| 4.42 | 4-CF$_3$ | H | NO$_2$ | CF$_3$ | |
| 4.43 | 3-NO$_2$ | Cl | CF$_3$ | NO$_2$ | |
| 4.44 | 3-NO$_2$ | H | NO$_2$ | CF$_3$ | |
| 4.45 | 5-NO$_2$ | Cl | CF$_3$ | NO$_2$ | |
| 4.46 | 5-NO$_2$ | H | NO$_2$ | CF$_3$ | |
| 4.47 | 5-Cl, 3-CF$_3$ | Cl | CF$_3$ | NO$_2$ | |
| 4.48 | 5-Cl, 3-CF$_3$ | H | NO$_2$ | CF$_3$ | |
| 4.49 | 6-CN, 3,4,5-Cl$_3$ | Cl | CF$_3$ | NO$_2$ | |
| 4.50 | 6-CN, 3,4,5-Cl$_3$ | H | NO$_2$ | CF$_3$ | |

TABLE 5

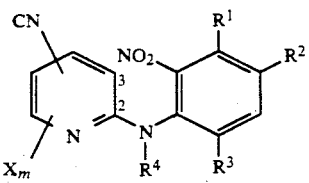

| No. | $X_m$/CN | $R^1$ | $R^2$ | $R^3$ | $R^4$ | m.p. (°C.) |
|---|---|---|---|---|---|---|
| 5.1 | 3-CN | Cl | CF$_3$ | NO$_2$ | SO$_2$C$_6$H$_5$ | |
| 5.2 | 3-CN | Cl | CF$_3$ | NO$_2$ | CH$_2$—CH=CH$_2$ | |
| 5.3 | 3-CN | Cl | CF$_3$ | NO$_2$ | CH$_2$—C≡CH | |
| 5.4 | 3-CN | H | NO$_2$ | CF$_3$ | COCH$_2$Cl | |
| 5.5 | 5-CN | Cl | CF$_3$ | NO$_2$ | SO$_2$C$_6$H$_5$ | |
| 5.6 | 5-CN | Cl | CF$_3$ | NO$_2$ | CONH$_2$ | |
| 5.7 | 5-CN | H | NO$_2$ | CF$_3$ | COOCH$_2$C$_6$H$_5$ | |
| 5.8 | 5-CN | H | NO$_2$ | CF$_3$ | SO$_2$C$_6$H$_5$ | |
| 5.9 | 3-Cl, 5-CN | H | H | Cl | SO$_2$C$_6$H$_5$ | |
| 5.10 | 3-Cl, 5-CN | Cl | CF$_3$ | NO$_2$ | CH$_2$—CH=CH$_2$ | |
| 5.11 | 3-Cl, 5-CN | Cl | CF$_3$ | NO$_2$ | CH$_2$—C≡CH | |
| 5.12 | 3-Cl, 5-CN | H | CF$_3$ | H | SO$_2$C$_6$H$_5$ | 147–158 |
| 5.13 | 3-Cl, 5-CN | Cl | CF$_3$ | NO$_2$ | SO$_2$C$_6$H$_5$ | |
| 5.14 | 3-Cl, 5-CN | Cl | CF$_3$ | NO$_2$ | COCH$_3$ | |

TABLE 5-continued

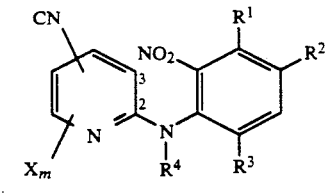

| No. | $X_m$/CN | $R^1$ | $R^2$ | $R^3$ | $R^4$ | m.p. (°C.) |
|---|---|---|---|---|---|---|
| 5.15 | 3-Cl, 5-CN | Cl | CF$_3$ | NO$_2$ | COCHCl$_2$ | |
| 5.16 | 3-Cl, 5-CN | Cl | CF$_3$ | NO$_2$ | COC$_6$H$_5$ | |
| 5.17 | 3-Cl, 5-CN | Cl | CF$_3$ | NO$_2$ | COOCH$_3$ | |
| 5.18 | 3-Cl, 5-CN | Cl | CF$_3$ | NO$_2$ | CONH$_2$ | |
| 5.19 | 3-Cl, 5-CN | Cl | CF$_3$ | NO$_2$ | CHO | |
| 5.20 | 3-Cl, 5-CN | H | NO$_2$ | CF$_3$ | SO$_2$C$_6$H$_5$ | |
| 5.21 | 3-Cl, 5-CN | H | NO$_2$ | CF$_3$ | COOCH$_3$ | |
| 5.22 | 3-Cl, 5-CN | H | NO$_2$ | CF$_3$ | COCH$_2$Cl | |
| 5.23 | 6-Cl, 3-CN | Cl | CF$_3$ | NO$_2$ | SO$_2$C$_6$H$_5$ | |
| 5.24 | 6-Cl, 3-CN | H | NO$_2$ | CF$_3$ | SO$_2$C$_6$H$_5$ | |
| 5.25 | 6-Cl, 5-CN | Cl | CF$_3$ | NO$_2$ | SO$_2$C$_6$H$_5$ | |
| 5.26 | 6-Cl, 5-CN | H | NO$_2$ | CF$_3$ | SO$_2$C$_6$H$_5$ | |
| 5.27 | 4-CH(CH$_3$)$_2$, 6-OC$_2$H$_5$, 3,5-(CN)$_2$ | Cl | CF$_3$ | NO$_2$ | SO$_2$C$_6$H$_5$ | |
| 5.28 | 4-CH(CH$_3$)$_2$, 6-OC$_2$H$_5$, 3,5-(CN)$_2$ | H | NO$_2$ | CF$_3$ | SO$_2$C$_6$H$_5$ | |
| 5.29 | 5-Cl, 3-CN | Cl | CF$_3$ | NO$_2$ | SO$_2$C$_6$H$_5$ | |
| 5.30 | 5-Cl, 3-CN | Cl | CF$_3$ | NO$_2$ | COOCH$_3$ | |
| 5.31 | 5-Cl, 3-CN | Cl | CF$_3$ | NO$_2$ | CONH$_2$ | |
| 5.32 | 5-Cl, 3-CN | Cl | CF$_3$ | NO$_2$ | COC$_6$H$_5$ | |
| 5.33 | 5-Cl, 3-CN | H | NO$_2$ | CF$_3$ | SO$_2$C$_6$H$_5$ | |
| 5.34 | 5-Cl, 3-CN | H | NO$_2$ | CF$_3$ | COOCH$_3$ | |
| 5.35 | 5-Cl, 3-CN | H | NO$_2$ | CF$_3$ | CONH$_2$ | |
| 5.36 | 5-Cl, 3-CN | H | NO$_2$ | CF$_3$ | COC$_6$H$_5$ | |
| 5.37 | 5-Cl, 3-CN | H | NO$_2$ | CF$_3$ | COCHCl$_2$ | |
| 5.38 | 6-cyclo-C$_3$H$_5$, 3-CN | Cl | CF$_3$ | NO$_2$ | SO$_2$C$_6$H$_5$ | |
| 5.39 | 6-CH$_3$, 3,5-(CN)$_2$ | Cl | CF$_3$ | NO$_2$ | SO$_2$C$_6$H$_5$ | |
| 5.40 | 6-CH$_3$, 3,5-(CN)$_2$ | H | NO$_2$ | CF$_3$ | SO$_2$C$_6$H$_5$ | |
| 5.41 | 6-Cl, 4-CN | Cl | CF$_3$ | NO$_2$ | SO$_2$C$_6$H$_5$ | |
| 5.42 | 6-Cl, 4-CN | H | NO$_2$ | CF$_3$ | SO$_2$C$_6$H$_5$ | |
| 5.43 | 4,6-(CH$_3$)$_2$, 3-CN | Cl | CF$_3$ | NO$_2$ | SO$_2$C$_6$H$_5$ | |
| 5.44 | 4,6-(CH$_3$)$_2$, 3-CN | H | NO$_2$ | CF$_3$ | SO$_2$C$_6$H$_5$ | |
| 5.45 | 4,6-(CH$_3$)$_2$, 3-CN | H | CH$_3$ | NO$_2$ | SO$_2$C$_6$H$_5$ | |

TABLE 6

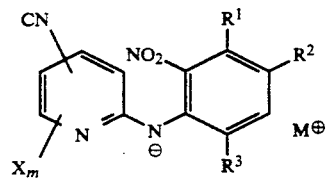

| No. | $X_m$/CN | $R^1$ | $R^2$ | $R^3$ | $M^+$ | m.p. (°C.) |
|---|---|---|---|---|---|---|
| 6.1 | 3-CN | Cl | CF$_3$ | NO$_2$ | K$^+$ | |
| 6.2 | 3-CN | Cl | CF$_3$ | NO$_2$ | N(CH$_3$)$_4$$^+$ | |
| 6.3 | 3-CN | Cl | CF$_3$ | NO$_2$ | N(C$_4$H$_9$)$_4$$^+$ | |
| 6.4 | 3-CN | Cl | CF$_3$ | NO$_2$ | C$_6$H$_5$—NH(CH$_3$)$_2$$^+$ | |
| 6.5 | 3-CN | Cl | CF$_3$ | NO$_2$ | NH(C$_2$H$_5$)$_3$$^+$ | |
| 6.6 | 3-CN | H | NO$_2$ | CF$_3$ | K$^+$ | |
| 6.7 | 3-CN | H | NO$_2$ | CF$_3$ | N(CH$_3$)$_4$$^+$ | |
| 6.8 | 3-CN | H | NO$_2$ | CF$_3$ | N(C$_4$H$_9$)$_4$$^+$ | |
| 6.9 | 5-CN | Cl | CF$_3$ | NO$_2$ | K$^+$ | |
| 6.10 | 5-CN | Cl | CF$_3$ | NO$_2$ | N(C$_4$H$_9$$_4$$^+$ | |
| 6.11 | 5-CN | H | NO$_2$ | CF$_3$ | N(C$_4$H$_9$)$_4$$^+$ | |
| 6.12 | 3-Cl, 5-CN | Cl | CF$_3$ | NO$_2$ | K$^+$ | 175 |
| 6.13 | 3-Cl, 5-CN | Cl | CF$_3$ | NO$_2$ | N(CH$_3$)$_4$$^+$ | 198 |

TABLE 6-continued

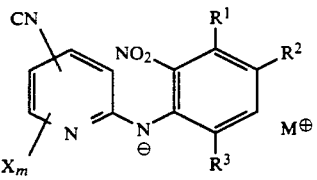

| No. | $X_m$/CN | $R^1$ | $R^2$ | $R^3$ | $M^+$ | m.p. (°C.) |
|---|---|---|---|---|---|---|
| 6.14 | 3-Cl, 5-CN | Cl | $CF_3$ | $NO_2$ | $N(C_4H_9)_4{}^+$ | 110–112 |
| 6.15 | 3-Cl, 5-CN | Cl | $CF_3$ | $NO_2$ | $NH_2(i\text{-}C_3H_7)_2$ | 92–94 |
| 6.16 | 3-Cl, 5-CN | Cl | $CF_3$ | $NO_2$ | $(CH_3)_3NCH_2CH_2OH^+$ | |
| 6.17 | 3-Cl, 5-CN | H | $NO_2$ | $CF_3$ | $K^+$ | |
| 6.18 | 3-Cl, 5-CN | H | $NO_2$ | $CF_3$ | $N(C_4H_9)_4{}^+$ | |
| 6.19 | 3-Cl, 5-CN | H | $NO_2$ | $CF_3$ | $NH_2(i\text{-}C_3H_7)_2{}^+$ | |
| 6.20 | 3-Br, 5-CN | Cl | $CF_3$ | $NO_2$ | $N(C_4H_9)_4{}^+$ | |
| 6.21 | 3-Br, 5-CN | H | $NO_2$ | $CF_3$ | $N(C_4H_9)_4{}^+$ | |
| 6.22 | 5-Cl, 3-CN | Cl | $CF_3$ | $NO_2$ | $K^+$ | |
| 6.23 | 5-Cl, 3-CN | Cl | $CF_3$ | $NO_2$ | $N(C_4H_9)_4{}^+$ | |
| 6.24 | 5-Cl, 3-CN | H | $NO_2$ | $CF_3$ | $K^+$ | |
| 6.25 | 5-Cl, 3-CN | H | $NO_2$ | $CF_3$ | $N(C_4H_9)_4{}^+$ | |
| 6.26 | 5-Br, 3-CN | Cl | $CF_3$ | $NO_2$ | $N(C_4H_9)_4{}^+$ | |
| 6.27 | 5-Br, 3-CN | H | $NO_2$ | $CF_3$ | $N(C_4H_9)_4{}^+$ | |
| 6.28 | 6-Cl, 3-CN | Cl | $CF_3$ | $NO_2$ | $N(C_4H_9)_4{}^+$ | |
| 6.29 | 6-Cl, 3-CN | H | $NO_2$ | $CF_3$ | $N(C_4H_9)_4{}^+$ | |
| 6.30 | 4-$CH(CH_3)_2$, 6-$OC_2H_5$, 3,5-$(CN)_2$ | Cl | $CF_3$ | $NO_2$ | $N(C_4H_9)_4{}^+$ | |
| 6.31 | 4-$CH(CH_3)_2$, 6-$OC_2H_5$, 3,5-$(CN)_2$ | H | $NO_2$ | $CF_3$ | $N(C_4H_9)_4{}^+$ | |
| 6.32 | 6-$CH_3$, 3,5-$(CN)_2$ | Cl | $CF_3$ | $NO_2$ | $N(C_4H_9)_4{}^+$ | |
| 6.33 | 6-$CH_3$, 3-CN | Cl | $CF_3$ | $NO_2$ | $N(C_4H_9)_4{}^+$ | |
| 6.34 | 6-cyclo-$C_3H_5$, 3-CN | Cl | $CF_3$ | $NO_2$ | $N(C_4H_9)_4{}^+$ | |
| 6.35 | 6-Cl, 4-CN | Cl | $CF_3$ | $NO_2$ | $N(C_4H_9)_4{}^+$ | |
| 6.36 | 6-Cl, 4-CN | H | $NO_2$ | $CF_3$ | $N(C_4H_9)_4{}^+$ | |
| 6.37 | 4,6-$(CH_3)_2$, 3-CN | Cl | $CF_3$ | $NO_2$ | $N(C_4H_9)_4{}^+$ | |
| 6.38 | 4,6-$(CH_3)_2$, 3-CN | H | $NO_2$ | $CF_3$ | $N(C_4H_9)_4{}^+$ | |
| 6.39 | 4,6-$(CH_3)_2$, 3-CN | H | $CH_3$ | $NO_2$ | $N(C_4H_9)_4{}^+$ | |
| 6.40 | 6-$CH(CH_3)_2$, 3-CN | Cl | $CF_3$ | $NO_2$ | $N(C_4H_9)_4{}^+$ | |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals,
*Rhizoctonia* species in cotton and lawns,
*Ustilago* species in cereals and sugar cane,
*Venturia inaequalis* (scab) in apples,
*Helminthosporium* species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Fusarium* and *Verticillium* species in various plants,
*Plasmopara viticola* in grapes,
*Alternaria* species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1.239 is mixed with 10 parts by weight of N-methyl-α-pyrrolidone. A mixture is obtained which is suitable for application in the form of very fine drops.

II. 20 parts by weight of compound no. 1.207 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 3.19 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1.239 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 1.226 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 1.223 is intimately mixed with 97 parts by weight of particulate kaolin. A dust is obtained containing 3% by weight of the active ingredient.

VII. 30 parts by weight of compound no. 1.234 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1.200 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 1.93 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the compounds according to the invention may be combined is intended to illustrate, and not restrict, the combination possibilities.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;

nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide, N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide, 2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

For comparison purposes, 2-(2,4-dinitro-6-trifluoromethylanilino)-5-trifluoromethylpyridine (A) disclosed in EP-A 31,257 was used.

USE EXAMPLE 1

Action on *Plasmopara viticola*

Leaves of potted vines of the Müller-Thurgau variety were sprayed with aqueous liquors containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 1.197, 1.200, 1.207, 1.223, 1.226, 1.234, 1.239 and 3.19, applied as 0.05 wt % spray liquors, have a better fungicidal action (95-100%) than prior art comparative active ingredient A (70%).

USE EXAMPLE 2

Action on *Botrytis cinerea* in pimientos

Pimiento seedlings of the "Neusiedler Ideal Elite" variety with 4 to 5 well developed leaves were sprayed to runoff with aqueous suspensions containing (dry basis) 80% of active ingredient and 20% of emulsifier. After the sprayed-on layer had dried, the plants were sprayed with a conidial suspension of the fungus Botrytis cinerea and kept in a high-humidity chamber at 22° to 24° C. After 5 days, the disease had spread on the untreated control plants to such an extent that the necroses covered the major portion of the leaves.

The results show that active ingredients 1.93 and 3.19, applied as 0.05 wt % spray liquors, have a better fungicidal action (85-95%) than prior art active ingredient A (0%).

We claim:
1. A 2-anilinocyanopyridine of the formula I

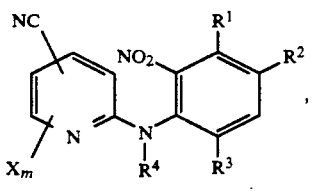

where
X is H, NO₂, CN, halogen, SO₂—C₁-C₄-alkyl, C₁-C₄-alkyl, C₃-C₆-cycloalkyl, C₁-C₄-haloalkyl, C₁-C₄-alkoxy, phenoxy, phenoxy substituted from one to three times with halogen or from one to two times with nitro or methyl, phenylthio or phenylthio substituted from one to three times with halogen or from one to two times with nitro or methyl,
m is an integer from 1 to 3, with the individual radicals being identical or different when m is greater than 1, 1. $R^1$ is hydrogen, halogen, $C_1$-$C_4$-alkoxy, $C_1$-$C_4$-haloalkyl, $C_1$-$C_4$-haloalkoxy, phenoxy, phenoxy substituted from one to three times with halogen or from one to two times with nitro or methyl, phenylthio or phenylthio substituted from one to three times with halogen or from one to two times with nitro or methyl, $R^2$ and $R^3$ are, independently of one another, hydrogen, $NO_2$, halogen, CN, $C_1$-$C_6$-alkyl, $SO_2$-$C_1$-$C_4$-alkyl, $C_1$-$C_6$-haloalkyl, $SO_2NR^5R^6$, $C_1$-$C_4$-haloalkoxy, $COOR^5$ or $CONR^5R^6$, $R^4$ is hydrogen, $COOR^7$, $CONR^5R^6$, CHO, $COR^7$, $SO_2R^7$, $C_3$-$C_6$-alkenyl or $C_3$-$C_6$-alkynyl, $R^5$ and $R^6$ are, independently of one another, hydrogen or $C_1$-$C_4$-alkyl, $R^7$ is $C_1$-$C_4$-alkyl, $C_1$-$C_4$-haloalkyl, benzyl, phenyl, 2-tolyl, 3-tolyl, 4-tolyl, halophenyl, nitrophenyl, 1-naphthyl or 2-naphthyl, or a salt of said 2-anilinocyanopyridine of the formula I in which $R^4$ is hydrogen with a plant-tolerated cation.

2. A compound of the formula I as set forth in claim 1, where $X_m$ is 4-isopropyl, 3-cyano, 5-cyano, 6-ethoxy, $R^1$ is chlorine, $R^2$ is trifluoromethyl, $R^3$ is nitro and $R^4$ is hydrogen.

3. A compound of the formula I as set forth in claim 1, where $X_m$ is 3-chloro, 5-cyano, $R^1$ is hydrogen, $R^2$ is trifluoromethyl, $R^3$ is hydrogen and $R^4$ is benzenesulfonyl.

4. The A 2-anilinocyanopyridine of claim 1, wherein m is an integer from 1 to 2.

5. A fungicidal composition comprising a fungicidally effective amount of a compound of the formula I where X is H, $NO_2$, CN, halogen, $SO_2$-$C_1$-$C_4$-alkyl, $C_1$-$C_4$-alkyl, $C_3$-$C_6$-cycloalkyl, $C_1$-$C_4$-haloalkyl, $C_1$-$C_4$-alkoxy, phenoxy, phenoxy substituted from one to three times with halogen or from one to two times with nitro or methyl, phenylthio or phenylthio substituted from one to three times with halogen or from one to two times with nitro or methyl, m is an integer from 1 to 3, with the individual radicals being identical or different when m is greater than 1, $R^1$ is hydrogen, halogen, $C_1$-$C_4$-alkoxy, $C_1$-$C_4$-haloalkyl, $C_1$-$C_4$-haloalkoxy, phenoxy, phenoxy substituted from one to three times with halogen or from one to two times with nitro or methyl, phenylthio or phenylthio substituted from one to three times with halogen or from one to two times with nitro or methyl, $R^2$ and $R^3$ are, independently of one another, hydrogen, $NO_2$, halogen, CN, $C_1$-$C_6$-alkyl, $SO_2$-$C_1$-$C_4$-alkyl, $C_1$-$C_6$-haloalkyl, $SO_2NR^5R^6$, $C_1$-$C_4$-haloalkoxy, $COOR^5$ or $CONR^5R^6$, $R^4$ is hydrogen, $COOR^7$, $CONR^5R^6$, CHO, $COR^7$, $SO_2R^7$, $C_3$-$C_6$-alkenyl or $C_3$-$C_6$-alkynyl, $R^5$ and $R^6$ are, independently of one another, hydrogen or $C_1$-$C_4$-alkyl, $R^7$ is $C_1$-$C_4$-alkyl, $C_1$-$C_4$-haloalkyl, benzyl, phenyl, 2-tolyl, 3-tolyl, 4-tolyl, halophenyl, nitrophenyl, 1-naphthyl or 2-naphthyl, or a salt of said 2-anilinocyanopyridine of the formula I in which $R^4$ is hydrogen with a plant-tolerated cation in admixture with a suitable inert carrier.

6. The fungicidal composition of claim 5, wherein m is an integer from 1 to 2.

7. A method for combating fungi, comprising applying a fungicidally effective amount of a compound of the formula where X is H, $NO_2$, CN, halogen, $SO_2$-$C_1$-$C_4$-alkyl, $C_1$-$C_4$-alkyl, $C_3$-$C_6$-cycloalkyl, $C_1$-$C_4$-haloalkyl, $C_1$-$C_4$-alkoxy, phenoxy, phenoxy substituted from one to three times with halogen or from one to two times with nitro or methyl, phenylthio or phenylthio substituted from one to three times with halogen or from one to two times with nitro or methyl, m is an integer from 1 to 3, with the individual radicals being identical or different when m is greater than 1, $R^1$ is hydrogen, halogen, $C_1$-$C_4$-alkoxy, $C_1$-$C_4$-haloalkyl, $C_1$-$C_4$-haloalkoxy, phenoxy, phenoxy substituted from one to three times with halogen or from one to two times with nitro or methyl, phenylthio or phenylthio substituted from one to three times with halogen or from one to two times with nitro or methyl, $R^2$ and $R^3$ are, independently of one another, hydrogen, $NO_2$, halogen, CN, $C_1$-$C_6$-alkyl, $SO_2$-$C_1$-$C_4$-alkyl, $C_1$-$C_6$-haloalkyl, $SO_2NR^5R^6$, $C_1$-$C_4$-haloalkoxy, $COOR^5$ or $CONR^5R^6$, $R^4$ is hydrogen, $COOR^7$, $CONR^5R^6$, CHO, $COR^7$, $SO_2R^7$, $C_3$-$C_6$-alkenyl or $C_3$-$C_6$-alkynyl, $R^5$ and $R^6$ are, independently of one another, hydrogen or $C_1$-$C_4$-alkyl, $R^7$ is $C_1$-$C_4$-alkyl, $C_1$-$C_4$-haloalkyl, benzyl, phenyl, 2-tolyl, 3-tolyl, 4-tolyl, halophenyl, nitrophenyl, 1-naphthyl or 2-naphthyl, or a salt of said 2-anilinocyanopyridine of the formula I in which $R^4$ is hydrogen with a plant-tolerated cation to a locus subject to fungal infection.

8. The method for combating fungi of claim 7, wherein m is an integer from 1 to 2.

* * * * *